US005798491A

United States Patent [19]

Magda et al.

[11] Patent Number: 5,798,491
[45] Date of Patent: Aug. 25, 1998

[54] MULTI-MECHANISTIC CHEMICAL CLEAVAGE USING CERTAIN METAL COMPLEXES

[75] Inventors: Darren Magda, Cupertino, Calif.; Jonathan L. Sessler, Austin, Tex.

[73] Assignees: Board of Regents, The University of Texas System, Austin, Tex.; Pharmacyclics, Inc., Sunnyvale, Calif.

[21] Appl. No.: 458,347

[22] Filed: Jun. 2, 1995

Related U.S. Application Data

[63] Continuation-in-part of Ser. No. 452,261, May 26, 1995, abandoned, and Ser. No. 310,501, filed as PCT/US94/06284, Jun. 9, 1994, Pat. No. 5,567,687, each is a continuation-in-part of Ser. No.227,370, Apr. 14, 1994, Pat. No. 5,559,207, which is a continuation-in-part of Ser. No. 75,123, Jun. 9, 1993, abandoned.

[51] Int. Cl.⁶ .................................................. C07B 61/00
[52] U.S. Cl. ............................ 204/157.15; 204/157.68; 435/91.1
[58] Field of Search ..................... 204/157.15, 157.68; 435/91.1

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,120,411 | 6/1992 | Sessler et al. | 204/157.15 |
| 5,141,911 | 8/1992 | Meunier et al. | 502/159 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | 534/11 |
| 5,457,195 | 10/1995 | Sessler et al. | 540/472 |
| 5,543,514 | 8/1996 | Sessler et al. | 540/472 |

(List continued on next page.)

FOREIGN PATENT DOCUMENTS

| | | |
|---|---|---|
| 0111418 | 6/1984 | European Pat. Off. |
| 0196515 | 10/1986 | European Pat. Off. |
| 0214908 A1 | 3/1987 | European Pat. Off. |
| 0233702 A2 | 8/1987 | European Pat. Off. |
| 2697254 | 4/1994 | France |
| WO 90/02747 | 3/1990 | WIPO |
| 90/01208 | 8/1990 | WIPO |
| WO 90/10633 | 9/1990 | WIPO |
| 91/19730 | 12/1991 | WIPO |
| 92/01781 | 2/1992 | WIPO |
| WO 93/14093 | 7/1993 | WIPO |
| 94/09003 | 4/1994 | WIPO |
| WO 94/29316 | 12/1994 | WIPO |
| WO 95/21845 | 8/1995 | WIPO |
| WO 95/29702 | 11/1995 | WIPO |
| WO 96/07667 | 3/1996 | WIPO |
| WO 96/09315 | 3/1996 | WIPO |

OTHER PUBLICATIONS

PCT Search Report mailed Feb. 23, 1995.
International Search Report mailed Dec. 6, 1994.
International Search Report mailed Feb. 22, 1994.
International Search Report mailed Feb. 3, 1994.

(List continued on next page.)

*Primary Examiner*—Cecelia J. Tsang
*Assistant Examiner*—C. Delacroix-Muirheid
*Attorney, Agent, or Firm*—Akin, Gump, Strauss, Hauer & Feld, L.L.P.

[57] ABSTRACT

The invention is directed to a particular class of metal complexes, specifically certain texaphyrin metal complexes, which both hydrolyze and photocleave RNA, and which also both hydrolyze RNA and photocleave DNA.

In one embodiment, the present invention is directed to a method for both hydrolyzing and photocleaving a polymer of ribonucleic acid, the method comprising the steps of contacting the polymer of ribonucleic acid with a texaphyrin metal complex exhibiting catalytic activity for both hydrolysis and photocleavage of ribonucleic acid polymers, incubating the polymer and the metal complex under conditions and for a time sufficient to hydrolyze the phosphate ester bond of the polymer, and exposing the texaphyrin metal complex to light for a time sufficient to photocleave the polymer.

In another embodiment of the present invention, the invention is directed to a method for both hydrolyzing a polymer of ribonucleic acid and photocleaving a polymer of deoxyribonucleic acid, the method comprising the steps of contacting a mixture of the ribonucleic acid polymer and the deoxyribonucleic acid polymer with a texaphyrin metal complex exhibiting catalytic activity for both hydrolysis of ribonucleic acid polymers and photocleavage of deoxyribonucleic acid polymers, incubating the polymer mixture and the metal complex under conditions and for a time sufficient to hydrolyze the phosphate ester bond of the ribonucleic acid polymer, and exposing the texaphyrin metal complex to light for a time sufficient to photocleave the deoxyribonucleic acid polymer.

27 Claims, 1 Drawing Sheet

U.S. PATENT DOCUMENTS

| | | | |
|---|---|---|---|
| 5,559,207 | 9/1996 | Sessler et al. | 530/300 |
| 5,565,552 | 10/1996 | Magda et al. | 534/11 |
| 5,567,687 | 10/1996 | Magda et al. | 514/44 |
| 5,587,371 | 12/1996 | Sessler et al. | 514/185 |
| 5,587,478 | 12/1996 | Sessler et al. | 540/474 |
| 5,594,136 | 1/1997 | Sessler et al. | 540/472 |
| 5,595,726 | 1/1997 | Magda et al. | 424/9.61 |
| 5,599,923 | 2/1997 | Sessler et al. | 540/145 |
| 5,599,928 | 2/1997 | Hemmi et al. | 540/474 |
| 5,607,924 | 3/1997 | Magda et al. | 514/44 |
| 5,622,946 | 4/1997 | Sessler et al. | 514/185 |

OTHER PUBLICATIONS

Abid et al., "Lanthanide Complexes of Some Macrocyclic Schiff Bases Derived from Pyridine-2,6-dicarboxaldehyde and α, ω-Primary Diamines", Inorg. Chim. Acta, 95:119-125, 1984.

Acholla et al., "Binucleating Tetrapyrrole Macrocycles", J. Am. Chem. Soc., 107:6902-6908, 1985.

Acholla et al., "A Binucleating Accordian Tetrapyrrole Macrocycle", Tetrahedron Lett., 25:3269-3270, 1984.

Ansell, "X-Ray Crystal Structure of the Pentagonal Bipyramidal Nickel (11) Complex $[Ni^{11}(L)(H_2O)_2](BF_4)_2$ and the Selective Stabilisation of the Nickel (1) Oxidation State by a Quinquedentate Macrocyclic Ligand", J. Chem. Soc., Chem. Commun. pp. 546-547, 1982.

Bauer et al., "Sapphyrins: Novel Aromatic Pentapyrrolic Macrocyces", J. Am. Chem. Soc., 105:6429-6436, 1983.

Broadhurst et al., "Preparation of Some Sulphur-containing Polypyrrolic Macrocycles. Sulphur Extrusion from a meso-Thiaphlorin", J. Chem. Soc., Chem. Commun. pp. 807-809, 1970.

Broadhurst et al., "18-and 22-π-Electron Macrocycles Containing Furan, Pyrrole, and Thiophren Rings", J. Chem. Soc., Chem. Commn. pp. 1480-1482, 1969.

Broadhurst et al., "New Macrocyclic Aromatic Systems Related to Porphins", J. Chem. Soc., Chem. Commun. pp. 23-24, 1969.

Broadhurst et al., "The Synthesis of 22 π-Electron Macrocycles. Sapphyrins and Related Compounds", J. Chem. Soc. Perkin Trans., 1:2111-2116, 1972.

Cuellar et al., "Synthesis and Characterization of Metallo and Metal-Free Octaalkylphthalocyanines and Uranyl Decaalkysuperphthalocyanines", Inorg. Chem., 20:3766-3770, 1981.

Day et al., "Large Metal Ion-Centered Template Reactions. A Uranyl Complex of Cyclopentakis (2-iminoisoindoline)", J. Am. Chem. Soc., 97:4519-4527, 1975.

De Cola et al., "Hexaaza Macrocyclic Complexes of the Lanthanides", Inorg. Chem., 25:1729-1732, 1986.

Dougherty, "Photosensitizers: Therapy and Detection of Malignant Tumors", Photochem. Photobiol., 45:879-889, (1987).

Gosmann et al., "Synthesis of a Fourfold Enlarged Porphyrin with an Extremely Large, Diamagnetic Ring-Current Effect", Angew. Chem., Int. Ed Engl., 25:1100-1101, (1986).

Gossauer, "Syntheses of Some Unusual Polypyrrole Macrocycles", Bull. Soc. Chim. Belg., 92:793-795, (1983).

Knubel et al., "Biomimetic Synthesis of an Octavinylogous Porphyrin with an Aromatic [34] Annulene System", Angew. Chem., Int. Ed. Engl., 27:1170-1172, 1988.

Lauffer, "Paramagnetic Metal Complexes as Water Proton Relaxation Agents for NMR Imaging: Theory and Design", Chem. Rev., 87:901-927, 1987.

LeGoff et al., "Synthesis of a |1,5,1,5| Platyrin, a 26 π-Electron Tetrapyrrolic Annulene", J. Org. Chem. 52:710-711, 1987.

Marks et al., "Large Metal Ion-Centered Template Reactions. Chemical and Spectral Studies of the Superphthalocyanine Dioxocyclopentakis (1-iminoisoindolinato) uranium (VI) and Its Derivatives", J. Am. Chem. Soc., 100:1695-1705, 1978.

Rexhausen et al., "The Synthesis of a New 22 π-Electron Macrocycle: Pentaphyrin", J. Chem. Soc., Chem. Commun., p. 275, 1983.

Sessler et al., "Synthesis and Crystal Structure of a Novel Tripyrrane-Containing Porphyrinogen-like Macrocycle", J. Org. Chem., 52:4394-4397, 1987.

Sessler et al., "The Coordination Chemistry of Planar Pentadentate Porphyrin-Like Ligands", Comm. Inorg. Chem., 7:333-350, 1988.

Sessler et al., "An Expanded Porphyrin: The Synthesis and Structure of a New Aromatic Pentadentate Ligand", J. Am. Chem. Soc., 110:5586-5588, 1988.

Tweedle et al., "Principles of Contrast-Enhanced MRI. in Magnetic Resonance Imaging," 2nd ed. Partain, et al, Eds., W. B. Saunders: Philadelphia, vol. I (1988) 793-809.

Vogel et al., "Porphycene -a Novel Porphin Isomer", Angew. Chem., Int. Ed. Engl., 25:257-259, 1986.

Vogel et al., "2,7,12,17-Tetrapropylporphycene -Counterpart of Octaethylporphyrin in the Porphycene Series", Angew. Chem., Int. Ed. Engl., 26:928-931, 1987.

Sessler et al., "A Water-Stable Gadolinium (III) Complex Derived from a New Pentadentate Expanded Porphyrin Ligand", Inorg. Chem., 28:3390-3393, 1989.

Sessler et al., "Binding of Pyridine and Benzimidazole to a Cadmium Expanded Porphyrin: Solution and X-ray Structural Studies", Inorg. Chem., 28:1333-1341, 1989.

Harriman et al., "Metallotexaphyrins: A New Family of Photosensitisers for Efficient Generation of Singlet Oxygen", J. Chem. Soc., Chem. Commun., 314-316, 1989. Submitted as A32 in 1449 for UTSB:458.

Sessler et al., "Expanded Porphyrins: The synthesis and Metal Binding Properties of Novel Tripyrrane-Containing Macrocycles", J. Coord. Chem., 18:99-104, 1988.

Sessler et al., "The Synthesis and Structure of a Novel 22 π-Electron Aromatic Pentadentate Macrocyclic Ligand: An Expanded Prophyrin", Toronto ACS Meeting, Jun. 1988. USA.

Sessler et al., "A Water-Stable Gadolinium (III) Complex Derived from a New Pentadentate", Chem. Absts., 111:720, abstract no. 125716e, Oct. 2, 1989.

Stinson, "Unusual Porphyrin Analog Promises Many Applications", Chemical and Engineering News, pp. 26-27, Aug. 8, 1988.

Sessler et al., "Tripyrroledimethine-derived (Texaphyrin--type) Macrocycles: Potential Photosensitizers Which Absorb in the Far-red Spectral Region", SPIE, Optical Methods for Tumor Treatment and Early Diagnosis: Mechanism and Technique, 1426:318-329, 1991.

Sessler et al., "'Texaphyrin': A Novel 22 π-Electron Aromatic Pentadentate Macrocyclic Ligand", ACS meeting, Los Angeles. Sep. 1988.

Sessler and Burrell, "Expanded Porphyrins," Topics in Current Chemistry, 161:180-273, 1991.

Sessler et al., "Synthesis and Structural Characterization of Lanthanide (III) Texaphyrins," Inorganic Chemistry, 32(14):3175-3187, 1993.

Beilstein, "2-Äthylamino-2-methyl-propanol-(1)", *Beilstein's Handbuch*, 4:785, 1950.

Fasman, "Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, 1992, Washington, DC.

Sessler, Jonathan L., "Texas–Sized Molecule," *Discovery*, 13(1):44–49, 1993.

Sessler et al., "Photodynamic Inactivation of Enveloped Viruses Using Sapphyrin, a 22 π–Electron Expanded Porphyrin: Possible Approaches to Prophylactic Blood Purification Protocols," *SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. Am. Chem. Soc.*, 1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine–and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysys," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalcator Group, and a Catalytic Site," *J. Chem. Soc. Chem. Commun.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Kimura, et al., "Macrocyclic Polyamines as Biological Cation and Anion Complexones –An Application to Calculi Dissolution," *Topics in Current Chemistry, 128, Biomimetic and Bioorganic Chemistry VII* +265P, Springer–Verlag, Berlin, West Germany, pp. 113, 142, 1985.

Li and Diederich, "Carriers for Liquid Membrane Transport of Nucleotide 5'–Triphosphates," *J. Org. Chem.* 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato) uranium(VI) and Its Derivatives," *J. Am. Chem. Soc.*, 1978, 1695–1705.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases –Superiority of Macrobicyclid Host Molecules," *Angew. Chem. Int. Ed. Engl.*, 1991, 30(4):442–444.

Sessler et al., "Anion Binding: A New Direction in Porphyrin–Related Research," *Pure & Applied Chem.*, 65(3):393–398, 1993.

Sessler et al., "Synthesis and Binding Properties of Monomeric and Dimeric Guanine and Cytosine Amine Derivatives," *J. Org. Chem.*, 1992, 47:826–834.

Aoyama et al., "Multi–Point Interaction of Phosphates with Protonated Pyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

Wang et al., "Pyrrole chemistry. XVII. Alkylation of the pyrrolyl ambident anion," *Can. J. Chem.*, 55:4112–4116, 1977.

Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (II) Texaphyrin: A Novel MRI Contrast Agent," *Journal of the American Chemical Society*, 115(22):10,368–10, 369, 1993.

Iverson et al., "Interactions Between Expanded Porphyrins and Nucleic Acids," *Pure Applied Chemistry*, 66(4):845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE–Int. Soc. Opt. Eng* 1992, 1645 (Proc. Opt. Methods Tumor Treat. Dect.: Mech. Tech. Photodyn. Ther. . . , 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA·Fe(II)," *Proc. Natl. Acad. Sci. USA*, 82:968–972, 1985.

Le Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Le Doan et al., "Targeted Cleavage of Polynucleotides by Complementary Oligonucleotides Covalently Linked to Iron–Prophyrins," *Biochemistry*, 26:6736–6739, 1986.

Dervan, Peter B., "Design of Sequence–Specific DNA–Binding Molecules," *Science*, 232:464–471, 1986.

Groves and Farrell, "DNA Cleavage by a Metal Chelating Tricationic Porphyrin," *J. Am. Chem. Soc.*, 111:4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides*, 10(1–3):641–643, 1991.

Zuk et al., "Pharmacokinetic and Tissue Distribution Studies of the Photosensitizer bis(Di–Isobutyl Octadecysiloxy) Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fullerene–Oligonucleotide Conjugates: Photo–Induced Sequence Specific DNA Cleavage", *Agnew. Chem. Int. Ed. Engl.*, 33(23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4):316–322, 1994.

Fedorova et al., "Palladium(II)–Coproporphyrin I as a Photoactivable Group in Seequence–Specific Modification of Nucleic Acids by Oligonucleotide Derivatives," *FEBS Lett.*, 259(2):335–337, 1990.

Morgan and Skalkos, "Second Generation Sensitizers: Where are We and Where Should We Be Going?" *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.*, 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*, 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA*, 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OEPc and EtioPc)–Tetra–and Pentacoordinated Zinc Complexes of OEPc," *Angew. Chem. Int. Ed. Engl.*, 32(11):1600–1604, 1993.

Wessel et al., "Porphyrins with Aromatic 26π–Electron Systems," *Agnew. Chem. Int. Ed. Eng.*, 32(8):1148–1151, 1993.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Breslow et al., "Effects of Metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack S., "Chemically Modified Oligodeoxynucleotide Analogs as Regulators of Viral and Cellular Gene Expression,"*Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with $(Lys)_2Cu$ as the Core Motif," *Journal of the Chemical Society*, 4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'–= Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication Mediated by Retroviral Vectors," *Gene Regulation: Biology of Antisense RNA and DNA*, 261–271, 1992.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site–Selective Hydrolysis of tRNA by Lanthanide Metal Complexes," *Inorg. Chem.*, 32:5899–5900, 1993.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates, in Transition Metals in Supramolecular Chemistry," L. Fabbrizzi and A. Poggi, Editors, NATO ASI Series, Kluwer, Amsterdam, pp. 391–408, 1994.

International Search Report mailed Feb. 9, 1996.

Cases et al., "Preparation of Hybrid DNA Cleaver–Oligonucleotide Molecules Based on a Metallotris (methylpyridiniumyl) porphyrin Motif," *Bioconjugate Chem.*, vol. 4, No. 5, pp. 366–371, Sep./Oct. 1993.

International Search Report for related foreign application PCT/US96/08262, date of mailing Sep. 10, 1996.

Magda, et al., "Texaphyrin–based nuclease analogs. Rationally designed approaches to the catalytic cleavage of RNA and DNA targets," *Chemical Abstracts* 125(7):5032 (Aug. 1996).

International Search Report for related foreign application PCT/US96/09419, date of mailing Dec. 17, 1996.

5'- YTxHN·(CH₂)₆PO₄-CAT CTG TGA GCC GGG TGT TG-3'  1_A  SEQ.ID NO.1
5'- YTxHN·(CH₂)₆PO₄-CTC GGC CAT AGC GAA TGT TC-3'  1_B  SEQ.ID NO.2
5'DyTxHN·(CH₂)₆PO₄-CAT CTG TGA GCC GGG TGT TG-3'  1_C  SEQ.ID NO.1
5'DyTxHN·(CH₂)₆PO₄-CTC GGC CAT AGC GAA TGT TC-3'  1_D  SEQ.ID NO.2
5'LuTxHN·(CH₂)₆PO₄-CAT CTG TGA GCC GGG TGT TG-3'  1_E  SEQ.ID NO.1
5'LuTxHN·(CH₂)₆PO₄-CTC GGC CAT AGC GAA TGT TC-3'  1_F  SEQ.ID NO.2

DNA 36-mer  3'- A AAT AAA ACC TCT GAA GTA GAC ACT CGG CCC ACA AC -5'  1_G  SEQ.ID NO.3

RNA 36-mer  3'- A AAU AAA ACC UCU GAA GUA GAC ACU CGG CCC ACA AC -5'  1_H  SEQ.ID NO.4

DNA 36-mer  3'- G CGC CAG AGA GGT GAG CCG GTA TCG CTT ACA AGA CA -5'  1_I  SEQ.ID NO.5

RNA 36-mer  3'- G CGC CAG AGA GGU GAG CCG GUA UCG CUU ACA AGA CA -5'  1_J  SEQ.ID NO.6

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:1:

CATCTGTGAG CCGGGTGTTG                                                20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:2:

CTCGGCCATA GCGAATGTTC                                                20

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:3:

CAACACCCGG CTCACAGATG AAGTCTCCAA AATAAA                      36

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA"

( x i ) SEQUENCE DESCRIPTION: SEQ ID NO:4:

CAACACCCGG CUCACAGAUG AAGUCUCCAA AAUAAA                      36

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (i i) MOLECULE TYPE: other nucleic acid
    (A) DESCRIPTION: /desc = "DNA"

(x i) SEQUENCE DESCRIPTION: SEQ ID NO:5:

ACAGAACATT CGCTATGGCC GAGTGGAGAG ACCGCG    3 6

(2) INFORMATION FOR SEQ ID NO:6:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "RNA"

(x i) SEQUENCE DESCRIPTION: SEQ ID NO:6:

ACAGAACAUU CGCUAUGGCC GAGUGGAGAG ACCGCG    3 6

MULTI-MECHANISTIC CHEMICAL CLEAVAGE USING CERTAIN METAL COMPLEXES

CROSS-REFERENCE TO RELATED APPLICATIONS

This application is a continuation-in-part application of patent applications U.S. Ser. No. 08/452,261 filed May 26, 1995 now abandoned and U.S. Ser. No. 08/310,501 filed Sep. 21, 1994, now U.S. Pat. No. 5,567,687. U.S. Ser. No. 08/452,261 is a continuation of, and U.S. Ser. No. 08/310,501 is a continuation-in-part application of PCT/US94/06284 filed Jun. 9, 1994, which is a continuation-in-part application of U.S. Ser. No. 08/227,370 filed Apr. 14, 1994, now U.S. Pat. No. 5,559,207. U.S. Ser. No. 08/227,370 is a continuation-in-part application of U.S. Ser. No. 08/075,123 filed Jun. 9, 1993, now abandoned.

FIELD OF THE INVENTION

This invention relates to methods for both catalytically hydrolyzing polymers of ribonucleic acid and photocleaving polymers of ribonucleic acid and polymers of deoxyribonucleic acid with a single agent.

BACKGROUND OF THE INVENTION

The texaphyrins are aromatic pentadentate macrocyclic "expanded porphyrins" which have been found to be useful as MRI contrast agents, as radiosensitizers and in photodynamic therapy (PDT). They have also shown activity in phosphate ester and RNA hydrolysis or in RNA and DNA light-induced cleavage, depending on the metal with which they are complexed. Texaphyrin is considered as being an aromatic benzannulene containing both 18π- and 22π-electron delocalization pathways. See, e.g., Sessler, J. L. et al., *Accounts of Chemical Research*, 1994, 27:43. Texaphyrin molecules absorb strongly in the tissue-transparent 730–900 nm range, and they exhibit inherent selective uptake or biolocalization in certain tissues, particularly regions such as, for example, liver, atheroma or tumor tissue. Texaphyrins and water-soluble texaphyrins, method of preparation and various uses have been described in U.S. Pat. Nos. 4,935,498; 5,252,720; 5,256,399; 5,272,142; and 5,292,414; and, U.S. Ser. Nos. 08/135,118 and 08/196,964; all of which are incorporated herein by reference. Texaphyrins may be coupled to site-directing molecules to form conjugates for targeted in vivo delivery. Site-specific ester hydrolysis of RNA with a paramagnetic metal texaphyrin complex-oligonucleotide conjugate has been shown; see, Magda, D. et al., *J. Am. Chem. Soc.*, 1994, 116:7439; and PCT publication WO 94/29316 (the entire disclosure of which is incorporated herein by reference). Site-specific light-induced photocleavage of DNA with a diamagnetic metal texaphyrin complex-oligonucleotide conjugate has also been carried out; see, Magda, D. et al., *J. Am. Chem. Soc.*, 1995, 117:3629; and U.S. Ser. No. 08/310,501 (the entire disclosure of which is incorporated herein by reference).

While many texaphyrin metal complexes have been shown to promote the hydrolysis of phosphate ester bonds (see, WO 94/29316), and at the same time, other texaphyrin metal complexes have been shown to act as catalysts for the light-induced cleavage (photocleavage) of DNA and RNA (see, U.S. Ser. No. 08/310,501), it has not been previously shown that a single texaphyrin metal complex would both hydrolyze and photocleave RNA, or would both hydrolyze RNA and photocleave DNA. Such a texaphyrin complex would be very useful in practical terms, since only one metal complex would be necessary to perform a variety of functions. This is especially important in in vivo treatment situations where it is desirable for only a relatively small amount of material to be present. It is also desirable where the metal complex itself, such as for example where the complex is an oligonucleotide conjugate, is quite expensive or can be produced in only small quantities. Additionally, while two separate conjugates could be employed to cover both photocleavage and hydrolysis activities, respectively, the conjugates would compete with one another.

SUMMARY OF THE INVENTION

The inventors have now discovered a particular class of texaphyrin metal complexes which both hydrolyzes and photocleaves RNA. This class of complexes also both hydrolyzes RNA and photocleaves DNA.

In particular, in one embodiment, the present invention is directed to a method for both hydrolyzing and photocleaving a polymer of ribonucleic acid, the method comprising the steps of contacting the RNA polymer with a texaphyrin metal complex having catalytic activity for both hydrolysis and photocleavage of RNA polymers, incubating the RNA polymer and the metal complex under conditions and for a time sufficient to hydrolyze the phosphate ester bond of the polymer, and exposing the texaphyrin metal complex to light for a time sufficient to photocleave the RNA polymer.

In another embodiment of the present invention, the invention is directed to a method for both hydrolyzing a polymer of ribonucleic acid and photocleaving a polymer of deoxyribonucleic acid, the method comprising the steps of contacting a mixture of the ribonucleic acid polymer and the deoxyribonucleic acid polymer with a texaphyrin metal complex having catalytic activity for both hydrolysis of RNA polymers and photocleavage of DNA polymers, incubating the polymer mixture and the metal complex under conditions and for a time sufficient to hydrolyze the phosphate ester bond of the ribonucleic acid polymer, and exposing the texaphyrin metal complex to light for a time sufficient to photocleave the deoxyribonucleic acid polymer.

BRIEF DESCRIPTION OF THE DRAWINGS

The drawing shows the yttrium(III) texaphyrin (YTx) DNA conjugates, dysprosium(III) texaphyrin (DyTx) DNA conjugates and lutetium(III) texaphyrin (LuTx) DNA conjugates of Example 1, and complementary 5'-$^{32}$P-labeled DNA 36-mers and 5'-$^{32}$P-labeled RNA 36-mers.

DETAILED DESCRIPTION OF THE INVENTION AND THE PREFERRED EMBODIMENTS

The present invention discloses the use of a single texaphyrin metal complex to perform two separate chemical reactions. Specifically, the texaphyrin metal complex exhibits the ability to catalyze both hydrolysis and photocleavage reactions. In one reaction, a phosphate ester bond is cleaved by hydrolysis; that is, the cleavage is a hydrolytic reaction where a water molecule is added across an ester bond to break the bond. This hydrolytic reaction is particularly useful for cleaving the phosphate ester bonds of a polymer of RNA, and is not dependent on the presence or absence of light. The second reaction, by comparison, is a photolytic cleavage reaction; that is, the texaphyrin metal complex, when irradiated in the presence of oxygen serves to produce cytotoxic materials, such as singlet oxygen, which products then cause strand damage or breakage, or "photocleavage".

of a polymer of DNA or RNA. Not wanting to be bound by theory, it is possible that singlet oxygen attacks a purine base, such as guanine for example, and causes depurination of double-stranded DNA similar to the Maxam and Gilbert chemical cleavage of DNA. It is important to note that while strand breakage, as outlined herein, is useful for quantitating the extent of photochemically derived damage, this damage in itself (e.g., modification of a nucleotide) is known to inhibit biological function of the biopolymer (for example, translation of RNA, phage infectivity). This photocleavage reaction is dependent on the presence of light, and in particular light in the spectral range of about 700 to 800 nm, where living tissues are relatively transparent.

The ability of a single agent to catalyze both types of cleavage reactions is especially useful in the design of therapy treatments which take advantage of both hydrolysis and photocleavage mechanisms. Thus, for example, a single texaphyrin metal complex can be targeted to a particular RNA, such as an antisense texaphyrin complex-oligonucleotide conjugate directed to a target mRNA. This metal complex-conjugate is administered to a patient, after which light is applied in proximity to the metal complex and the target mRNA to cause photocleavage of the RNA. The texaphyrin complex is not destroyed during the photocleavage reaction, so that after the light is removed, the complex-conjugate remains to cleave, via light-independent hydrolysis, any target RNA which may remain. In a second example, a single texaphyrin metal complex can be used in the cleavage and destruction of two different targets, one RNA-based and the other DNA-based, via hydrolytic and photocleavage action. In contrast to using two agents, each targeting either RNA or DNA only, the use of one agent to target both RNA and DNA precludes the reduction in efficiency, caused by the presence of two competing agents. Additionally, less total drug needs to be utilized to effect the desired result.

The methods of the present invention are conducted under conditions sufficient to hydrolyze the RNA and photocleave the DNA or RNA. Such conditions are known to those of skill in the art or can be determined by such persons without undue experimentation. It has been found that such conditions include physiologic conditions. This is especially useful when the texaphyrin complexes are used in vivo as a treatment procedure to hydrolyze RNA and also photocleave RNA or DNA.

In the practice of the present invention, the texaphyrin macrocycle to be complexed to the metal ion may be chosen from any texaphyrin molecule, including those now known and disclosed in the U.S. patents and patent applications incorporated by reference herein. Representatives of texaphyrin metal complexes included within the present invention are encompassed within the following formula:

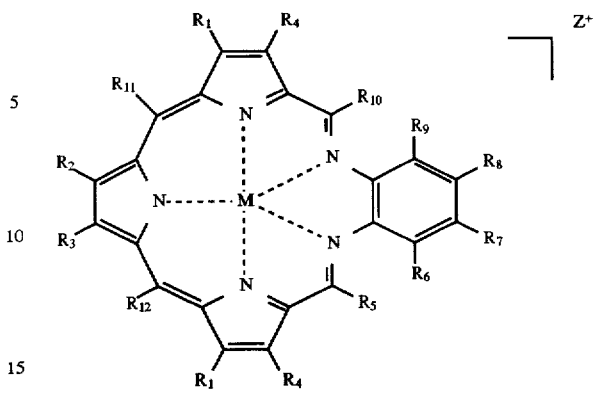

M is a divalent metal cation or a trivalent metal cation exhibiting catalytic activity for both hydrolysis of RNA polymers and photocleavage of RNA or DNA polymers. Metals useful in the present invention may include, but are not necessarily limited to, cadmium(II), yttrium(III), indium (III), lanthanum(III), lutietium(III), and other diamagnetic metal cations.

$R_1-R_4$, $R_7$ and $R_8$ are independently hydrogen, halide, hydroxyl, alkyl, alkenyl, alkynyl, aryl, haloalkyl, nitro, formyl, acyl, hydroxyalkyl, oxyalkyl, oxyhydroxyalkyl, hydroxyalkenyl, hydroxyalkynyl, saccharide, carboxy, carboxyalkyl, carboxyamide, carboxyamidealkyl, amino, aminoalkyl, a site-directing molecule, a catalytic group, or a couple to a site-directing molecule or to a catalytic group.

$R_6$ and $R_9$ are independently selected from the groups of $R_1-R_4$, $R_7$ and $R_8$, with the proviso that the halide is other than iodide and the haloalkyl is other than iodoalkyl.

$R_5$ and $R_{10}-R_{12}$ are independently hydrogen, alkyl, alkenyl, alkynyl, aryl, hydroxyalkyl, oxyalkyl, oxyhydroxyalkyl, hydroxyalkenyl, hydroxyalkynyl, carboxyalkyl, carboxyamide, carboxyamidealkyl, amino, aminoalkyl, or a couple to a saccharide, to a site-directing molecule or to a catalytic group.

The charge, Z, is an integer value less than or equal to 5. In the context of the basic macrocycle with a yttrium cation, Z is 1 or 2. However, one skilled in the art in light of the present disclosure would realize that the charge Z would be altered so as to account for the choice of metal M, the pH under consideration, and charges present on any of substituents $R_1-R_{12}$ and charges present on any covalently bound site-directing molecule, for example charges of the phosphate groups on an oligonucleotide. For instance, if $R_1$=carboxyl and $R_2-R_{12}$=alkyl and the metal M=Lu$^{+3}$, and the solution is pH=7 (so that $R_1$=CO$_2$—), the charge Z would be zero. The charge would be negative when substituents have a sufficient number of negative charges, for example, when a substituent is an oligonucleotide. The charge would be +5, for example, when the M is Lu$^{+3}$ and the net charge of a substituent(s) is three positive charges.

"Alkyl" means alkyl groups, straight, branched or cyclic isomers, with generally one to fifty, preferably one to thirty, more preferably one to ten, carbon atoms.

"Alkenyl" means alkenyl groups, straight, branched or cyclic isomers, with generally two to fifty, preferably two to thirty, more preferably two to ten, carbon atoms, and with one to five or more double bonds, preferably one to five, more preferably one to three double bonds.

"Alkynyl" means alkenyl groups, straight, branched or cyclic isomers, with generally two to fifty, preferably two to thirty, more preferably two to ten, carbon atoms, and with one to five or more triple bonds, preferably one to five, more preferably one to three triple bonds.

"Hydroxyalkyl" means alcohols of alkyl groups. Preferred are hydroxyalkyl groups having one to twenty, more preferably one to ten, hydroxyls. "Hydroxyalkyl" is meant to include polyethers with one or more functional groups; diols of alkyls, with diols of $C_{1-10}$ alkyls being preferred, and diols of $C_{1-3}$ alkyls being more preferred; and polyethylene glycol, polypropylene glycol and polybutylene glycol as well as polyalkylene glycols containing combinations of ethylene, propylene and butylene.

"Oxyalkyl" means alkyl groups as herein described with oxygen atoms, including ether linkages. The number of repeating oxyalkyls within a substituent may be up to 200, preferably from 1 to 20, more preferably from 1 to 7, and most preferably is 2–3. A preferred oxyalkyl is $O(CH_2CH_2O)_xCH_3$ where x=1–100, preferably 1–10, and more preferably, 2–3.

"Hydroxyalkoxy" means alkyl groups as described herein having ether or ester linkages, as well as hydroxyl groups, substituted hydroxyl groups, carboxyl groups, substituted carboxyl groups or the like.

"Carboxy" groups include carboxylic acids of the alkyls described herein as well as aryl carboxylic acids such as benzoic acid. "Carboxyalkyl" means alkyl groups having hydroxyl groups, carboxyl or amide substituted ethers, ester linkages, tertiary amide linkages removed from the ether or the like. Representative examples of "carboxyamides" include primary carboxyamides ($CONH_2$), and secondary (CONHR') and tertiary (CONR'R") carboxyamides where each of R' and R" is a functional group as described herein. "Carboxyamidealkyl" means alkyl groups with hydroxyl groups, secondary or tertiary amide linkages or the like.

Representatives of useful amines include a primary, secondary or tertiary amine of an alkyl as described hereinabove.

"Aryl" is an aromatic group, such as a benzyl or a phenyl group for example, unsubstituted or substituted with a nitro, carboxy, sulfonic acid, hydroxy, oxyalkyl, or halide.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of various sugars, and the like. Examples of amine-derivatized sugars are galactosamine, glucosamine, and sialic acid.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether, or the like.

For the above texaphyrins, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10; x is zero or a positive integer less than or equal to n; and y is zero or a positive integer less than or equal to ((2n+1)−2x).

The oxyhydroxyalkyl or saccharide may be $C_nH_{((2n+1)-q)}O_yR^a{}_q$, $OC_nH_{((2n+1)-q)}O_yR^a{}_q$ or $(CH_2)_nCO_2R^a$ where n is a positive integer from 1 to 10; y is zero or a positive integer less than or equal to ((2n+1)−q); q is zero or a positive integer less than or equal to (2n+1); and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{(2m+1)-2w)}O_wO_z$, where m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zR^b{}_r$ where m is a positive integer from 1 to 10, z is zero or a positive integer less than ((2m+1)−r), r is zero or a positive integer less than or equal to 2m+1, and $R^b$ is H, alkyl, hydroxyalkyl, or saccharide.

The carboxyamidealkyl may be $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10; $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zR^b{}_r$ where m is a positive integer from 1 to 10, z is zero or a positive integer less than ((2m+1)−r), r is zero or a positive integer less than or equal to 2m+1, and $R^b$ is H, alkyl, hydroxyalkyl, or saccharide.

The carboxyalkyl may be $C_nH_{((2n+1)-q)}O_yR^c{}_q$ or $OC_nH_{(2n+1)-q)}O_yR^c{}_q$ where n is a positive integer from 1 to 10; y is zero or a positive integer less than or equal to ((2n+1)−q); q is zero or a positive integer less than or equal to (2n+1); and $R^c$ is $(CH_2)_nCO_2R^d$, $(CH_2)_nCONHR^d$, or $(CH_2)_nCON(R^d)_2$ where n is a positive integer from 1 to 10, and $R^d$ is H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zR^b{}_r$ where m is a positive integer from 1 to 10, z is zero or a positive integer less than ((2m+1)−r), r is zero or a positive integer less than or equal to 2m+1, and $R^b$ is H, alkyl, hydroxyalkyl, or saccharide.

Hydrolytic cleavage of phosphate ester bonds, and particularly of RNA, by texaphyrin complexes may be enhanced by additional catalytic groups appended to the texaphyrin complex or to a texaphyrin complex-site directing molecule conjugate. The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and texaphyrin metal complexes. The term "appended to the texaphyrin complex-site directing molecule conjugate" means that the catalytic groups are attached either directly to the texaphyrin metal complex or to the texaphyrin complex via a linker or couple of variable length, or are attached to the ligand portion of a texaphyrin complex-ligand conjugate either with or without a linker or couple of variable length.

Exemplary site-directing molecules useful herein include, but are not limited to, polydeoxyribonucleotides, oligodeoxyribonucleotides, polyribonucleotide analogs, oligoribonucleotide analogs, polyamides including peptides having affinity for a biological receptor and proteins such as antibodies, steroids and steroid derivatives, hormones such as estradiol or histamine, hormone mimics such as morphine, and further macrocycles such as sapphyrins and rubyrins.

The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates, phosphoramidates and the like. Deoxyribonucleotides, deoxyribonucleotide analogs and ribonucleotide analogs are contemplated as site-directing molecules in the present invention.

The term "texaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directing molecule may be attached either directly to the texaphyrin or to the texaphyrin via a linker or a couple of variable length. During catalysis, for example, the texaphyrin portion of a texaphyrin metal complex-oligonucleotide conjugate is placed in the vicinity of the substrate upon binding of the oligonucelotide to the targeted nucleic acid substrate.

A conjugated group having site specificity or catalytic activity may be covalently coupled to a texaphyrin directly on the macrocycle ring or through various couples. A couple may be described as a linker, i.e., the covalent product formed by reaction of a reactive group designed to attach covalently another molecule at a distance from the texaphyrin macrocycle. Exemplary linkers or couples are amides, amine, disulfide, thioether, ether, ester, or phosphate covalent bonds. In preferred embodiments, conjugates and appended groups are covalently bonded to the texaphyrin via a carbon—carbon, a carbon—nitrogen, a carbon—sulfur, or a carbon—oxygen bond, more preferred being a carbon—oxygen or a carbon—nitrogen bond.

In the practice of the present invention, in a preferred embodiment at least one of $R_1$–$R_{12}$ is a site-directing molecule or is a couple to a site-directing molecule. Also presently preferred are those compounds where $R_1$ is hydroxyalkyl and $R_2$, $R_3$, and $R_4$ are alkyl. $R_7$ and $R_8$ may be hydroxyalkoxy or oxyalkyl. Alternatively, $R_3$, $R_7$ or $R_8$ may be a site-directing molecule or a couple to a site-directing molecule. Preferred site-directing molecules are a hormone or an oligonucleotide, more preferably an oligonucleotide. The oligonucleotide may be a deoxyribonucleotide, a deoxyribonucleotide derivative or analog, or a ribonucleotide analog. A presently preferred ribonucleotide analog, for example, has alkyl groups, more preferably methyl groups, on the 2' oxygen of the ribose. A presently preferred deoxyribonucleotide analog is a phosphorothioate or a phosphoramidate.

In a further preferred texaphyrin complex of the present invention, $R_1$ is $(CH_2)_2CH_2OH$, $R_2$ and $R_3$ are $CH_2CH_3$, $R_4$ is $CH_3$, and $R_7$ and $R_8$ are $OCH_2CH_2CH_2OH$ or $R_7$ and $R_8$ are $O(CH_2CH_2O)_tCH_2CH_2OR'$ where t is zero to 10, preferably zero to 3, and R' is H or $CH_3$. Alternatively, $R_8$ is a site-directing molecule or a couple thereto, preferably an oligonucleotide or a couple thereto, more preferably $O(CH_2)_nCO$-oligonucleotide where n is 1–7 and preferably 1–3. Where $R_8$ is a site-directing molecule or a couple thereto, $R_7$ may be H, $OCH_3$ or one of the previously listed preferred substituents.

A presently preferred metal is yttrium(III).

Water-soluble texaphyrins are often preferred for the applications described herein, particularly when in vivo administration and treatment is contemplated. "Water-soluble" means soluble in aqueous fluids to about 1 mM or better. Such characteristics allow these texaphyrins to be useful in a biological environment. Improved water solubility can be achieved by, for example, substituents chosen from saccharides or hydroxylated substituents.

However, while the above-described texaphyrins are presently preferred compounds for use in the present invention, the invention is not limited thereto and any texaphyrin complex that exhibits activity both as a hydrolyzing agent for RNA polymers and as a photocleaving agent for RNA or DNA polymers may be useful in the practice of the invention.

The texaphyrin metal complexes of the present invention can be synthesized by procedures as described in the patents and applications previously incorporated herein by reference. For example, a nonaromatic texaphyrin of structure I is mixed together with a metal salt, a Brønsted base and an oxidant, in an organic solvent, and the mixture is allowed to react to form an aromatic texaphyrin metal complex. A preferred means is to stir the mixture at ambient temperature or to heat the mixture at reflux for at least two hours.

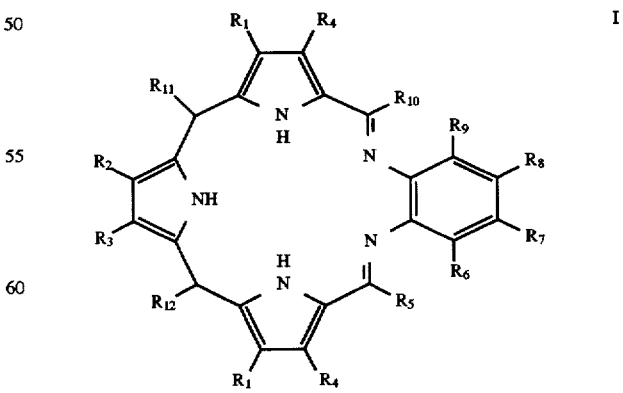

The nonaromatic texaphyrin I is conveniently produced by condensation of a tripyrrane aldehyde or ketone having structure A and a substituted orthophenylenediamine B:

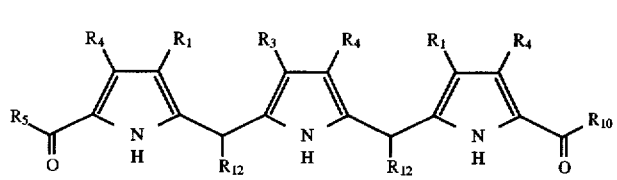

A

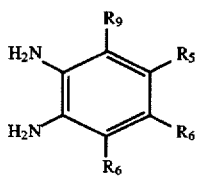

B

One skilled in the art of organic synthesis in light of the present disclosure and the disclosures in the patents, applications and publications incorporated by reference herein could extend and refine the above basic synthetic chemistry to produce texaphyrins having various substituents. For example, polyether-linked polyhydroxylated groups, saccharide substitutions in which the saccharide is appended via an acetal-like glycosidic linkage, an oligosaccharide or a polysaccharide may be similarly linked to a texaphyrin. A doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride p-nitrophenol acetate would generate activated acyl species suitable for attachment to monoclonal antibodies or other biomolecules of interest. Standard in situ coupling methods (e.g., 1,1'-carbonyldiimidazole) could be used to effect the conjugation.

The selectivity of the texaphyrins may be enhanced by covalently linking oligonucleotides onto the periphery of the macrocycle. Amides, ethers and thioethers are representative of linkages which may be used for this purpose. Oligonucleotides functionalized with amines at the 5'-end, the 3'-end, or internally at sugar or base residues may be modified post-synthetically with an activated carboxylic ester derivative of the texaphyrin complex. Alternatively, oligonucleotide analogs containing one or more thiophosphate or thiol groups may be selectively alkylated at the sulfur atom(s) with an alkyl halide derivative of the texaphyrin complex. The resultant oligonucleotide-complex conjugates may be designed so as to provide optimal catalytic interaction between a target nucleic acid and the bound texaphyrin. The oligonucleotide may be large enough to bind probably at least about 8 nucleotides of complementary nucleic acid. Specific methods for preparing texaphyrin-oligonucleotide conjugates are disclosed in WO 94/29316, previously incorporated herein by reference.

The use of texaphyrin complexes to hydrolyze RNA and also photocleave RNA or DNA in vivo as a treatment procedure relies on the effective localization of the complex to the site of desired cleavage. A site of desired cleavage may be a position novel to undesired organisms in terms of health care. A site of desired cleavage may be a DNA or an RNA encoding a product deleterious to the host or may be a normal DNA or RNA that is deleterious in some way. Treating native RNA or DNA with this new texaphyrin complex results in the texaphyrin complex binding to a complementary RNA or DNA sequence, respectively, via an appended oligonucleotide. The texaphyrin complex then cleaves the RNA or DNA proximal to this specific site. The binding of a conjugate to a DNA double helix will form a triple helix which has sufficient stability for effective cleavage to occur.

The texaphyrin complex-oligonucleotide conjugates of the present invention may be developed into antisense reagents. This antisense strategy provides a clear and rational method for new drug design because there is one requirement, namely that the antisense probe hybridize to its target molecule. The hybidization requirement is very well understood via complementary Watson-Crick or Hoogsteen base pairing. Unlike the present methods in the art which require screening of thousands of compounds and X-ray crystal structure analysis, the information needed for antisense technology is the sequence of the target. Treating native RNA or DNA with this texaphyrin complex-oligonucleotide conjugate results in the conjugate binding to a complementary RNA or DNA sequence, respectively, via the appended oligonucleotide. The texaphyrin complex then hydrolyzes and at the same time photocleaves the RNA, or hydrolyzes the RNA and photocleaves the DNA, as the case may be, proximal to this specific binding site. Attachment to the texaphyrin complex may cause the oligonucleotide antisense agent to take on some of the pharmacodynamic and biodistribution properties of the texaphyrin such as selective localization in tumors.

The texaphyrin-oligonucleotide conjugates may be useful for inhibiting the expression of a gene in an animal or in a particular tissue of an animal. They may also be useful in a method for targeted intracellular mRNA hydrolysis and photocleavage, or for targeted intracellular mRNA hydrolysis and DNA photocleavage.

The texaphyrin-oligonucleotide conjugates and present method of hydrolysis and photocleavage would have immediate applications for anti-viral and anti-bacterial therapy as well as cancers (an oligonucleotide complementary to an oncogene, for example) and inflammatory responses that are caused by the overexpression of certain proteins.

The following example is an illustration of the practice of the present invention, and is intended neither to define nor to limit the scope of the invention in any manner.

Example 1

The present example illustrates the site-specific, light-independent hydrolysis of RNA and the site-specific light-dependent photocleavage of DNA by yttrium(III) texaphyrin-DNA oligonucleotide conjugates. The RNA hydrolysis properties of the YTx conjugates are compared with those of analogous paramagnetic Dy(III)Tx conjugates, and the DNA photocleavage properties of the YTx conjugates are compared with those of analogous diamagnetic Lu(III)Tx conjugates.

The texaphyrin-oligonucleotide conjugate in each case had the following formula, where M is yttrium, dysprosium or lutetium:

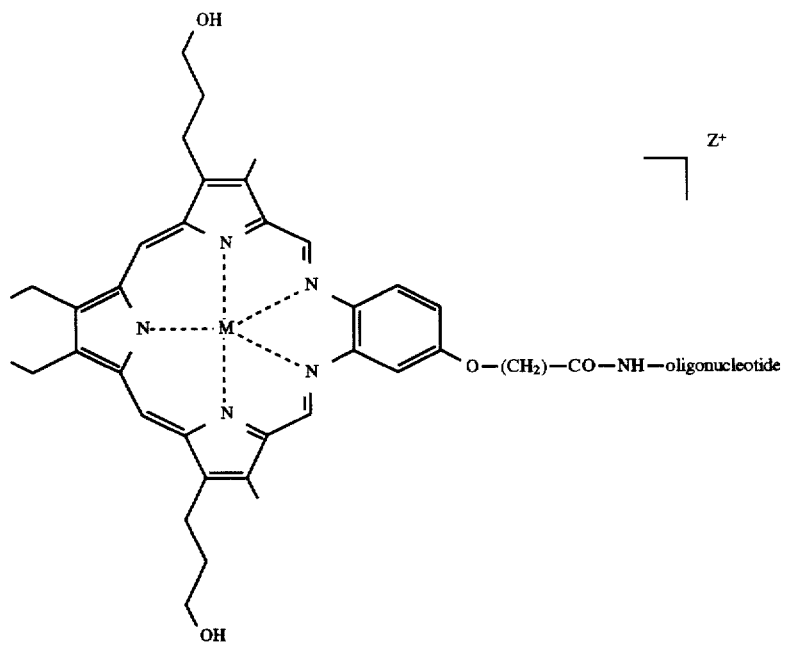

Methods for the preparation of the above texaphyrins, as well as those of other texaphyrins and texaphyrin-oligonucleotide conjugates, are described in WO 94/29316, the disclosure of which is incorporated herein by reference. The texaphyrin-oligonucleotide conjugates used in this Example are set out in the drawing. The DNA sequences used in the conjugates were purchased from Keystone Labs, Menlo Park, Calif.; and the RNA sequences were purchased from Promega Corp., Madison, Wis.

Reaction mixtures were prepared by adding YTx conjugate $1_A$ or $1_B$, DyTx conjugate $1_C$ or $1_D$, or LuTx conjugate $1_E$ or $1_F$ to solutions made from ca. 100,000 cpm of 5'-$^{32}$P-labeled DNA 36-mer $1_G$ or $1_H$ or 5'-$^{32}$P-labeled RNA 36-mer $1_I$ or $1_J$ mixed with 4× buffer (5 µL), carrier DNA (1 µL) and water to produce a final volume of 20 µL. Final conjugate concentration was 50 nM. The 4× buffer was 400 mM NaCl, 200 mM HEPES, pH 7.5, 100 µM EDTA. All reactions were heated for 4 minutes at 58° C. and allowed to cool slowly to ambient temperature.

RNA hydrolysis reactions were covered and incubated at 37° C. for 22 hr. DNA photocleavage reactions were irradiated for 15 min. at ambient temperature using a dye laser (Coherent, Palo Alto, Calif.) tuned to 732 nm using a power density of 150 mW/cm$^2$.

At the end of the reaction time, the reaction samples containing radiolabeled DNA were precipitated with ethanol, then were dissolved in 10% aqueous piperidine solution (50 µL) and heated to 90° C. for 30 min. Water (500 µL) was added to the DNA samples, which were then dried on a Speedvac. The samples from the RNA hydrolysis reactions were precipitated with ethanol using standard methods. All samples were resuspended in 50% formamide loading buffer, denatured at 60° C. for 3 min., and analyzed by electrophoresis on a 20% denaturing polyacrylamide gel.

The autoradiograph indicated substantial cleavages only in those lanes which contained the appropriate complementary 20-mer YTx, DyTx, or LuTx conjugate. All cleavages occurred near the expected location of the YTx, DyTx, or LuTx complex upon hybridization of the conjugates with their targets. The cleavage locations on the 36-mers are indicated by arrows in the drawing. The YTx- and LuTx-mediated DNA cleavage bands co-migrated with bands generated by dimethylsulfate in the guanine-specific sequencing lanes. The cleavage patterns generated by the YTx and DyTx conjugates on RNA were similar. Cleavage patterns generated by the YTx and LuTx conjugates on DNA were essentially identical. The total efficiency of RNA hydrolysis by the YTx conjugates ranged from 25–35%. The total efficiency of DNA photocleavage by the YTx conjugates ranged from 50–60%.

These observations are consistent with a model whereby hybridization of the YTx conjugates to complementary sequences of DNA effects site-specific photomodification of guanine residues, and results in site-specific photocleavage upon workup under basic conditions. By contrast, in a dark reaction, the YTx conjugates effect site-specific hydrolysis of complementary RNA targets. Thus, the YTx-DNA conjugates were able to damage nucleic acids by two distinct mechanisms, hydrolysis and photocleavage. Further, as conjugates containing LuTx, a diamagnetic metallotexaphyrin analogous to YTx, have previously been shown to effect site-specific photocleavage of both DNA and RNA targets, the above data imply that YTx conjugates would also effect site-specific photocleavage of RNA targets.

What is claimed is:

1. A method of both hydrolyzing and photocleaving a polymer of ribonucleic acid, the method comprising:
   contacting the polymer of ribonucleic acid with a texaphyrin metal complex that exhibits catalytic activity for both hydrolysis and photocleavage of ribonucleic acid polymers,
   incubating the polymer of ribonucleic acid and the metal complex under conditions and for a time sufficient to hydrolyze the phosphate ester bond of the polymer, and
   exposing the texaphyrin metal complex to light for a time sufficient to photocleave the polymer.

2. The method of claim 1 wherein the texaphyrin metal complex is a texaphyrin-diamagnetic metal complex.

3. The method of claim 1 wherein the texaphyrin metal complex is a yttrium-texaphyrin complex.

4. The method of claim 1 wherein the light has a wavelength range of about 700–800 nm.

5. The method of claim 1 wherein the step of exposing the texaphyrin metal complex to light is carried out in the presence of oxygen.

6. The method of claim 1 wherein the texaphyrin metal complex has the formula:

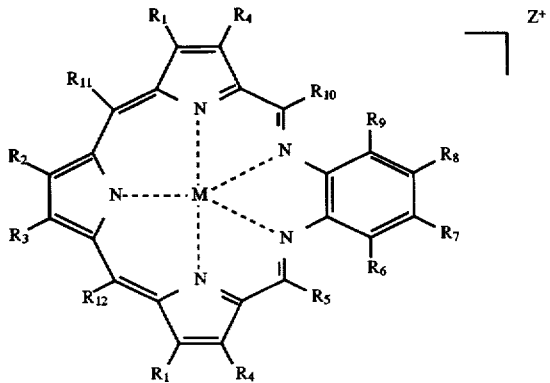

wherein,

M is a divalent metal cation or a trivalent metal cation exhibiting catalytic activity for both hydrolysis and photocleavage of RNA polymers;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, oxyalkyl, oxyhydroxyalkyl, hydroxyalkenyl, hydroxyalkynyl, saccharide, carboxy, carboxyalkyl, carboxyamide, carboxyamidealkyl, amino, aminoalkyl, a site-directing molecule, a catalytic group, or a couple to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, oxyalkyl, oxyhydroxyalkyl, hydroxyalkenyl, hydroxyalkynyl, carboxyalkyl, carboxyamide, carboxyamidealkyl, amino, aminoalkyl, or a couple to a saccharide, to a site-directing molecule or to a catalytic group; and Z is an integer value less than or equal to 5.

7. The method of claim 6 wherein M is yttrium(III).

8. The method of claim 6 wherein at least one of $R_1$–$R_{12}$ is a site-directing molecule, a catalytic group, a couple to a site-directing molecule or a couple to a catalytic group.

9. The method of claim 8 wherein the catalytic group is imidazole, guanidine, an amino acid, an amino acid derivative, a polyamino acid, an amine-substituted saccharide or a texaphyrin metal complex.

10. The method of claim 8 wherein the site-directing molecule is an oligonucleotide, a hormone, an antibody, a peptide having affinity for a biological receptor, or a sapphyrin molecule.

11. The method of claim 6 wherein at least one of $R_1$–$R_{12}$ is a site-directing molecule, and the site-directing molecule is an oligonucleotide, which oligonucleotide has binding affinity for RNA.

12. The method of claim 11 wherein the oligonucleotide is a derivatized oligonucleotide or an oligonucleotide analog.

13. The method of claim 12 wherein the derivatized oligonucleotide is selected from the group consisting of methylphosphonates, phosphotriesters, phosphorothioates, and phosphoramidates.

14. The method of claim 12 wherein the derivatized oligonucleotide is 2'-O-alkyl oligoribonucleotide.

15. The method of claim 11 wherein the oligonucleotide is an antisense oligonucleotide.

16. A method of both hydrolyzing a polymer of ribonucleic acid and photocleaving a polymer of deoxyribonucleic acid, the method comprising:

contacting a mixture of the ribonucleic acid polymer and the deoxyribonucleic acid polymer with a texaphyrin metal complex that exhibits catalytic activity for both hydrolysis of ribonucleic acid polymers and photocleavage of deoxyribonucleic acid polymers, incubating the polymer mixture and the metal complex under conditions and for a time sufficient to hydrolyze the phosphate ester bond of the ribonucleic acid polymer, and exposing the texaphyrin metal complex to light for a time sufficient to photocleave the deoxyribonucleic acid polymer wherein the metal is yttrium(III) or dysprosium(III).

17. The method of claim 16 wherein the light has a wavelength range of about 700–800 nm.

18. The method of claim 16 wherein the step of exposing the texaphyrin metal complex to light is carried out in the presence of oxygen.

19. The method of claim 16 wherein the texaphyrin metal complex has the formula:

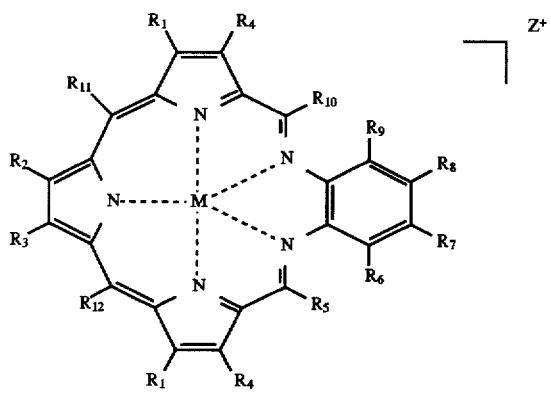

wherein,

M is yttrium(III) or dysprosium(III);

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, oxyalkyl, oxyhydroxyalkyl, hydroxyalkenyl, hydroxyalkynyl, saccharide, carboxy, carboxyalkyl, carboxyamide, carboxyamidealkyl, amino, aminoalkyl, a site-directing molecule, a catalytic group, or a couple to a site-directing molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, oxyalkyl, oxyhydroxyalkyl, hydroxyalkenyl, hydroxyalkynyl, carboxyalkyl, carboxyamide, carboxyamidealkyl, amino, aminoalkyl, or a couple to a saccharide, to a site-directing molecule or to a catalytic group; and Z is an integer value less than or equal to 5.

20. The method of claim 19 wherein M is yttrium(III).

21. The method of claim 19 wherein at least one of $R_1$–$R_{12}$ is a site-directing molecule, a catalytic group, a couple to a site-directing molecule or a couple to a catalytic group.

22. The method of claim 21 wherein the catalytic group is imidazole, guanidine, an amino acid, an amino acid derivative, a polyamino acid, an amine-substituted saccharide or a texaphyrin metal complex.

23. The method of claim 21 wherein the site-directing molecule is an oligonucleotide, a hormone, an antibody, a peptide having affinity for a biological receptor, or a sapphyrin molecule.

24. The method of claim 23 wherein the oligonucleotide is a derivatized oligonucleotide or an oligonucleotide analog.

25. The method of claim 24 wherein the derivatized oligonucleotide is selected from the group consisting of methylphosphonates, phosphotriesters, phosphorothioates, and phosphoramidates.

26. The method of claim 24 wherein the derivatized oligonucleotide is 2'-O-alkyl oligoribonucleotide.

27. The method of claim 23 wherein the oligonucleotide is an antisense oligonucleotide.

* * * * *

UNITED STATES PATENT AND TRADEMARK OFFICE
CERTIFICATE OF CORRECTION

PATENT NO. : 5,798,491
DATED : August 25, 1998
INVENTOR(S) : Magda, et al.

It is certified that error appears in the above-identified patent and that said Letters Patent is hereby corrected as shown below:

At [63] on the cover page, delete "Continuation-in-part of Ser. No. 452,261, May 26, 1995, abandoned, and Ser. No. 310,501, filed as PCT/US94/06284, Jun. 9, 1994, Pat. No. 5,567,687, each is a continuation-in-part of Ser. No. 227,370, Apr. 14, 1994, Pat. No. 5,559,207, which is a continuation-in-part of Ser. No. 75,123, Jun. 9, 1993, abandoned", and substitute -- continuation-in-part of Ser. No. 452,261, May 26, 1995, abandoned, which is a continuation of PCT/US94/06284, Jun. 9, 1994, and a continuation-in-part of Ser. No. 310,501, Sept. 21, 1994, Pat. No. 5,567,687, which is a continuation-in-part of PCT/US94/06284, Jun. 9, 1994, which is a continuation-in-part of Ser. No. 227,370, Apr. 14, 1994, Pat. No. 5,559,207, which is a continuation-in-part of Ser. No. 075,123, Jun. 9, 1993, abandoned--, therefor.

Signed and Sealed this

Nineteenth Day of January, 1999

Attest:

Attesting Officer

*Acting Commissioner of Patents and Trademarks*

UNITED STATES PATENT AND TRADEMARK OFFICE
CERTIFICATE OF CORRECTION

PATENT NO. : 5,798,491
DATED : August 25, 1998
INVENTOR(S) : Magda, et. al.

It is certified that error appears in the above-identified patent and that said Letters Patent is hereby corrected as shown below:

At column 1, immediately following the title, please insert the following paragraph:

-- The government may own certain rights in the present invention pursuant to one or more of the following: National Institutes of Health Grants CA68682, AI28845 and AI33577; and National Science Foundation Grants CHE8552768 and CHE9122161.--

Signed and Sealed this

Twenty-seventh Day of June, 2000

Attest:

Q. TODD DICKINSON

Attesting Officer

Director of Patents and Trademarks